United States Patent [19]

Guffroy

[11] Patent Number: 4,587,222
[45] Date of Patent: May 6, 1986

[54] REAGENT COMPRISING TREATED RED BLOOD CELLS AND METHODS FOR DETECTING RHEUMATOID FACTOR

[75] Inventor: René Guffroy, La Madeleine, France

[73] Assignee: Laboratories Polypharma, France

[21] Appl. No.: 394,151

[22] Filed: Jul. 1, 1982

Related U.S. Application Data

[63] Continuation of Ser. No. 234,559, Feb. 13, 1981, abandoned.

[30] Foreign Application Priority Data

Feb. 15, 1980 [FR] France ............................. 80 03440

[51] Int. Cl.$^4$ ............... G01N 33/555; G01N 33/556; G01N 33/564
[52] U.S. Cl. ......................................... 436/509; 424/3; 424/11; 436/520; 436/521; 436/805; 436/809
[58] Field of Search ..................... 424/3, 11, 13, 101; 436/509, 520, 805, 809, 521

[56] References Cited

U.S. PATENT DOCUMENTS

| | | | |
|---|---|---|---|
| 3,322,634 | 5/1967 | Fulthorpe | 436/521 |
| 3,548,051 | 12/1970 | Dingwall | 436/521 |
| 3,594,466 | 7/1971 | Guffroy | 436/521 |
| 3,708,572 | 1/1973 | Peetoom | 436/521 |
| 3,828,103 | 8/1974 | Fujita | 436/521 |
| 3,862,302 | 1/1975 | Price | 436/521 |

OTHER PUBLICATIONS

Milgrom, Arthritis & Rhev. vol. 7, 1964 pp. 1–7.
Williams, Method in Immunology and Immunochemistry, Acad. Press, New York, vol. 4, 1977, pp. 34–39.

Primary Examiner—Sidney Marantz
Attorney, Agent, or Firm—Larson and Taylor

[57] ABSTRACT

A reagent for the detection of rheumatoid factor in tests in tubes or microplates. The reagent contains a complex formed from red blood cells and from antibodies soluble with respect to these red blood cells, and immunologically fixed to the latter, said reagent being both stable and capable in given dilution intervals to give rise to hemagglutination only subject to contacting it with detectable concentrations of rheumatoid factor. The invention also relates to a process for making said reagent which comprises subjecting red cells and the antibodies to be fixed thereon to successive treatments with distinct aldehydes or tanning agents, as well as with proteinic substances, such as albumin, having dispersive properties. Finally the invention also provides a process for detecting the presence of rheumatoid factor in biological specimen which comprises contacting the latter with said reagent, whereby the response is positive or negative depending upon whether pattern hemagglutination or sedimentation of the cells of the complex is observed.

18 Claims, No Drawings

REAGENT COMPRISING TREATED RED BLOOD CELLS AND METHODS FOR DETECTING RHEUMATOID FACTOR

This is a continuation of the application Ser. No. 234,559, filed Feb. 13, 1981, now abandoned.

The invention relates to a novel reagent enabling the in vitro detection of the "rheumatoid factor" in serum or a similar biological specimen, the technique of detection itself, as well as a process for manufacturing this reagent.

It is known that the serum of patients afflicted with rheumatoid polyarthritis contains a globulin related to the β2 macroglobulin group which are called IgM macroglobulins.

This macroglobulin currently called "rheumatoid factor" is characterized in particular by its agglutinating properties with respect to complexes formed by red blood cells or red cells and antibodies, such as obtained from iso- or hetero-immunosera, previously formed against these red cells and taken in sub-agglutinating doses. These complexes are hence characterized by immunological linkages or "mutual antigen-antibody immunological bonds". The capacity of the rheumatoid factor to cause agglutination of this type of complex, is based on the WAALER-ROSE reaction or on reactions derived therefrom and which are considered as most specific for rheumatoid arthritis.

For clarity in the account which follows, it is proposed as from the outset to define the expressions "agglutination" and "hemagglutination" which will be referred to hereafter.

The expression "agglutination" will be used to denote the reaction visible to the naked eye which can be observed on a slide in the case of agglutination on a slide, when a reagent containing a complex such as defined above is placed in contact with a serum containing the rheumatoid factor. Of course one will also speak of "agglutination" when red cells are contacted with a sufficient dose of immunoserum to produce this agglutination reaction.

The expression "hemagglutination" will be used to denote a phenomenon such as that which results from the spontaneous formation of a "mat pattern" or "pattern agglutination", when red cells are contacted with a subagglutinating dilution of a corresponding immunoserum.

Two techniques are known in the art for the detection in vitro of the possible presence of the rheumatoid factor in a biological medium, for example a blood serum. They respectively bring into practice agglutination on slides" and "agglutinations in tubes or microplates".

The first technique (agglutination of slides) is easy to put into practice. The agglutination gives a rapid qualitative indication of the presence or not in the serum tested of the rheumatoid factor.

The second technique (agglutination in tubes or microplates) is capable of giving additionally quantitative approximations as to the content of rheumatoid factor of the tested serum, notably by means of the possible determination of the dilution-threshold which separates the less high dilution which still causes agglutination from the next higher dilution for which agglutination is no longer observed, instead only "hemagglutination".

It is well known that one of the difficulties encountered in the past as regards the tests on slides, and which in practice is not until now resolved in the case of tests in tubes or microplates, consists in the instability of the natural complexes formed by the globular antigens or red cells with antibodies of corresponding immunosera.

This difficulty has been overcome in the case of the reagents intended for slide-tests.

It is known that MILGROM and his collaborators (Arthritis and Rheumatism. 7 (1) pages 1 to 7 (1964) have proposed, in a first attempt to overcome the difficulties of applying the slide-test initially developed by WAALER and ROSE, of resorting to a complex formed from sheep's red blood cells which had previously been subjected to a treatment by a formaldehyde solution, such as formalin, hereafter referred to as "formalinization", and from rabbit anti-sheep red cell serum, taken at a dilution four times less than the highest dilution inducing, in titration in a tube, mat hemagglutination (in other words, a dilution four times less than the hemagglutination titer, as hereafter defined). According to MILGROM, the reagent obtained can be preserved for some time, notably two months, at 4° C., or in the frozen state, without appreciable loss of serological activity. Again according to these Authors, the reagent thus formed enables, when it is contacted on a slide with a human serum diluted twenty times in a sodium chloride isotonic buffer, the detection of the presence of the rheumatoid factor, by agglutination of this reagent when the rheumatoid factor is present, after keeping the mixture standing at ambient temperature for a period of from five to ten minutes.

Such a reaction however remains too slow in practice, especially if one takes into account the speed with which the liquid suspending medium tends to evaporate, from the moment when the mixture is placed on the slide.

U.S. Pat. No. 3,594,466 describes an improved reagent enabling this time an almost instantaneous reaction on a slide when the rheumatoid factor is present in the tested serum. It is characterized by the presence in the soluble antigen-antibody complex, of a much higher concentration of antibodies, which may be obtained by an improved process which consists of subjecting the complex previously formed between the immunoserum and the globular antigens, notably sheep's red blood cells (which may or may not have previously undergone formalinization or treatment by a similar aldehyde) to a stabilizing treatment with formaldehyde or a similar aldehyde. This improvement has an essential advantage in that the reagent formed is easy to use, the desired reaction, when it occurs, taking place before the mixture spread on the slide has had time to dry.

If the problem of producing an effective and stable reagent has been resolved satisfactorily as regards diagnostic tests on a slide in the presence or absence of the rheumatoid factor, this has not yet been achieved as regards the reagents used for the tests in tubes or microplates. In fact the reagents described in the literature and that are suitable for slide-test have the characteristics of giving rise spontaneously to the formation of pattern hemagglutination whether the rheumatoid factor is present or not. They are hence unsuitable in tests for the detection of the rheumatoid factor in sera liable of containing it.

It may also be mentioned that MILGROM hinted to preliminary tests putting into use formalinized red blood cells sensitized with a sub-hemagglutinating dilution of an anti-sheep rabbit serum. The technique that has been referred to cannot be brought into practice, if only because of the conditions in which MILGROM complex was obtained.

It is an object of the invention to overcome the foregoing difficulties, more particularly of providing a reagent both stabilized and selective for the detection of the rheumatoid factor in tests in tubes or microplates bringing into play hemagglutination.

It is also an object of the invention to develop a highly sensitive reagent enabling sensitive discrimination, on the one hand, of the rheumatoid factor possibly present, and on the other hand, of natural hetero-antibodies (such as anti-sheep red blood cells or FORSMAN antibodies) present in all human serums at relative high titers. The capacity possessed by these hetero-antibodies also of causing hemagglutinations with standard reagents is known. These hemagglutinations are liable of occuring, even if care has been taken to proceed with prior adsorption of the sera to be tested for the purpose of eliminating interfering antibodies. The invention therefore is more particularly directed to the object of developing a reagent for tests in tubes or microplates which can be applied without it generally being necessary to proceed at extreme dilution ranges of the serum and of subjecting it to prior adsorption of the interfering antibodies capable of masking the rheumatoid factor.

The reagent according to the invention for the detection of the rheumatoid factor in tests in tubes or microplates, containing a complex formed from red blood cells and from antibodies soluble with regard to these red blood cells, is characterized by both the stability and the capability in given dilution intervals to give rise to hemagglutination only subject to contacting it with detectable concentrations of rheumatoid factor, such as those contained in a biological medium originating from a patient afflicted by rheumatoid polyarthritis.

A preferred reagent according to the invention can also be defined as being characterized in that it contains a relative amount of antibodies conferring on said complex a sensitivity threshold with respect to the international standard serum of rheumatoid polyarthritis of the World Health Organization (WHO) of about 0.01 to about 1 IU/ml, notably from 0.05 to 0.30 IU/ml.

It may also be defined as being characterized by a detection threshold of the rheumatoid factor, in a serum diluted to 1/40th, of about 0.4 to about 40 IU/ml, such as from 2 to 12 IU/ml.

The invention also relates evidently to the use of the complex as defined above (or of a reagent containing that complex), if necessary previously diluted, to the detection of the rheumatoid factor or the like in a biological specimen, which use comprises contacting this complex (or this reagent) with this biological specimen, in particular a serum or an articular liquid, in tubes or microplates and detecting hemagglutination or sedimentation according as the serum contains the rheumatoid factor or not.

In most cases, this use can be practised directly on the biological specimen, if necessary previously diluted, notably at neutral pH, without first subjecting said specimen to absorption in order to eliminate the interfering antibodies.

According to the invention it has been observed that the presence of the rheumatoid factor is then revealed by the formation of hemagglutination, hence of a phenomenon similar in its manifestations to that which is observed with conventional agglutinating reagents, when they are contacted with biological media devoid of rheumatoid factor.

On the other hand, the absence of the rheumatoid factor in the serum tested or in other words the contacting of the reagent according to the invention with a "sub-agglutinating" dilution of the immunoserum, is manifested by a simple sedimentation of the complex cells, the latter then concentrating in the bottom of the tube. This "hemagglutination" or to the contrary this "sedimentation" are easily recognized when the abovementioned contacting is carried out in the tube elements of microplates currently used in laboratories. It is known that these tubes generally comprise an upper cylindrical portion terminating in a conical bottom. In the case of hemagglutination, it is possible to observe, after a certain time, the formation of a "mat pattern" or "pattern agglutination", generally coating substantially the whole of the conical bottom, whilst on the contrary, "sedimentation" is manifested by the concentration into a narrow button of the red cells at the extreme tip of these same tubes.

By "hemagglutination titer" will be meant hereafter the last dilution which, in a tube, leads to the formation of the abovementioned "mat pattern", that is to say the dilution preceding the larger one, for which "sedimentation" is then only observed.

If by "agglutination titer" one denotes the last dilution giving on a slide agglutinates visible to the naked eye, in other words, the dilution situated just before the first greater dilution which no longer induces the formation of said agglutinates, it is observed that the "hemagglutination titer" appears to be distinctly stronger than the "agglutination titer" in a ratio which, approximately, is higher than 10, for instance of the order of 40 in the case of an immunological complex of formalinized sheep red cells and of anti-sheep rabbit hemolytic serum.

The invention hence also relates to a reagent, such as defined above and which is in addition characterized by the fact that its hemagglutination titer and its agglutination titer are in a ratio of at least 10, notably of at least 20 in the case of a complex of sheep red cells and rabbit anti-sheep antibodies.

Preferred complexes according to the invention can also be defined as regards the relative content of antibodies they hold with respect to the maximum relative content which can be fixed on red cells not having undergone the treatment by the process according to the invention, as will be defined below, in the absence of hemagglutination. In particular, the relative content of antibodies of a preferred complex according to the invention is situated between about 2 and about 20, preferably about 3 and about 10 hemagglutinating units, it being understood that the hemagglutinating unit corresponds to the relative content of antibodies which can be retained by the corresponding red cells which have not undergone the treatment according to the invention, in the absence of hemagglutination.

The process according to the invention for obtaining the above-indicated complex comprises subjecting the red cells and the antibodies intended to be immunologically fixed on these red cells and originating from corresponding immunosera to:

a series of at least two successive treatments with two respectively distinct agents of the aldehyde or tanning agent type, and a third treatment by at least one dispersive substance notably of the protein type such as albumin, at least the first of the treatments with the aldehyde or tanning agents and the third treatment by the proteinic substance being carried out on red cells in the presence of antibodies intended to be fixed on these red cells.

The treatment with albumin or an equivalent substance can be carried out simultaneously with the last of the successive treatments of the abovesaid series, or separately as a final treatment.

It goes without saying that the relative proportions of the antibodies contacted with the red cells in the course of each of the abovementioned treatments, must each time be adjusted so as, on the one hand, to be compatible with the increased degree of stability which can be reached at the end of each of these treatments and, on the other hand, to permit the final obtaining of a reagent containing the desired relative proportions of antibodies fixed with respect to the red cells, notably the aboveindicated preferred proportions.

Advantageously, the agents of the aldehyde or tanning agent type are selected from among formic aldehyde, glutaraldehyde, pyruvic aldehyde, glyoxal, methylglyoxal or a similar aldehyde, the preferred agent being glutaraldehyde or again, as regards more particularly the tanning agents, tannic acid, vegetable and synthetic tannins, parabenzoquinone, sulfosalicylic acid, tanning substances of mineral origin such as chromium or zirconium salts, particularly chlorides, sodium silicate, sodium hyposulfite, etc. Generally, it is possible to resort to any stabilizing substance, non-destructive to red cells, and which can be recognized through its capacity to form with the hemoglobin of the red cells a combination resulting in chemical transformation of the hemoglobin, notably in the form of a brownish compound.

Preferred treatment conditions involve incubation at a temperature preferably above room temperature, which can reach 60° C. It is advantageously carried out at a temperature of the order of 37° C. and often, notably between 50° and 56° C. in the case of aldehydes.

In the following, the percentages are by volume, except where otherwise specified.

Preferably, the relative concentration of the treated red cells subjected to this treatment with respect to the medium in which they are incubated is from 1 to 10%, and the proportions of the aldehydes or of the tanning agents can vary in ranges which are to be determined in each case, notably from 0.2 to 1% for formaldehyde, 0.05 to 1.5% for glutaraldehyde, 0.25 to 2.5% for pyruvic aldehyde, 0.005 to 0.05% in weight for tannic acid, 0.025 to 0.25% in weight for hydrated chromium chloride $CrCl_3,6H_2O$.

The pH of the medium is advantageously from 5 to 9.5, preferably close to neutrality when recourse is had to treatments by aldehydes, and a little lower when recourse is had to tanning agents, for example, of the order of 5.5 when recourse is had to chromium salts.

As regards the second type of substance, there may be mentioned more particularly serum-albumin or other substances of the same albuminoid nature, the sera of other animal species or human serum, albumin fractions, $\alpha$ and $\beta$ globulins isolated from these sera, milk proteins, colloidal protein substances derived from collagen, such as purified gelatin, or colloidal substances of vegetable origin, such as gum arabic.

Generally it is possible to resort to any proteinic substance having dispersive properties or again substances capable of entering into competition with the sensitizing antibodies:

either by being fixed to the membrane of the red cells;

or by combining with the antibodies, notably when the treatment with such a substance is carried out simultaneously with the second of the treatments by an agent of the aldehyde type or by a tanning agent.

Recourse may again be had to other substances capable of playing a dispersing role, in particular in the sensitizing zone comprised between 2 and 5 hemagglutinating units of hemolytic serum; these are polyvinylpyrrolidone, for example that known under the designation SUBTOSAN emulsifiers of the anionic, cationic or non-ionic type.

Advantageously, the treatment with the proteinic and dispersing substance is carried out at a temperature above 37° C., preferably between 50° and 60° C. at a pH comprised between about 7 and about 9.2, particularly between 7 and 8.5 In the same way, the treatments with the aldehydes or tanning agents, or preferably the latter of these treatments, are carried out under the same conditions of temperature and pH. In the case where recourse is had to a final treatment of the red cells with the polyvinyl pyrrolidone or one of the abovementioned emulsifiers, it will be advantageous to operate at more alkaline pH's, which can reach 9.2. Advantageously, the proportion of red cells in the incubation medium is here again of the order of 1 to 10%, the relative concentration of dispersing substances being itself advantageously of the order of 0.5 to 5 g per liter.

These various treatments are carried out in suspension, the relative concentrations of the agents applied corresponding advantageously to those which are indicated below in the examples.

The invention takes advantage of the unexpected effects induced by the application of the process according to the invention which consist of the suppression of the spontaneous hemagglutination phenomena of the red cell-antibodies complexes obtained, and this up to relatively low dilutions in the absence of the rheumatoid factor, and of the appearance on the contrary of these hemagglutinating phenomena at much higher dilutions in the presence of a rheumatoid factor. The invention hence takes advantage of the great difference of the hemagglutination titers which can thus be measured, to discriminate between biological specimens depending whether they contain the rheumatoid factor or not. The process according to the invention also provides, besides stability, the possibility of obtaining reagents with a high content of antibodies, enabling consequently the selective discrimination of the rheumatoid factor possibly present with respect to the hetero-antibodies, anti-red cells of foreign origin or FORSMAN antibodies present in human sera.

The invention relates also to the compositions containing the complex as defined above, this composition containining preferably a proportion of 0.15 to 3, notably from 0.25 to 2.5% of the complex concerned in suspension in a buffer solution, particularly of pH 7.2 to 8.2. The solution may contain dispersing agents of the above type and/or conventional preserving agents such as that known as MERSEPTYL or sodium azide.

The invention relates finally to a method for detecting the rheumatoid factor or the like, which comprises contacting the complex as defined above with a serum or biological specimen to be studied, such as a serum or an articular fluid in tubes or the like and by the detection or not of dispersed hemagglutination according as the serum contains the rheumatoid factor or not. Particularly said method comprises repeating said contacts on increasing dilutions of said specimen.

The reagent and the serum or the like to be studied are if necessary previously diluted. Generally it is not necessary to carry out prior adsorption of the specimen to be tested in order to eliminate interfering antibodies therefrom.

The presence of the rheumatoid factor in the serum of the patient is manifested on the contrary by an absence of sedimentation. It is manifested by the formation of mat patterns of sensitized red cell after a few hours of contact in a buffer solution, notably at substantially neutral pH, at least up to a predetermined degree or dilution threshold. This degree or threshold also provides a quantitative indication as to the content of rheumatoid factor which can be present in the serum under study.

Additional characteristics of the invention will appear also in the course of the non-limiting description which follows of reagents according to the invention and of their modes of development.

(1) Selection of reagents

The complex according to the invention may be obtained from any red blood cell and from sensitizing hemolytic serum of any origin, such as those appearing by way of example in the table hereafter:

| Red blood cells | Sensitizing serums |
| --- | --- |
| A or B | Anti A or anti B iso-immuno-serum |
| O Rh + (CD)* | Anti-Rh serum |
| Sheep | Rabbit anti-sheep |
| Sheep | Rabbit anti-goat |
| Goat | Rabbit anti-sheep |
| Beef | Rabbit anti-beef |
| Guinea pig | Rabbit anti-guinea pig |
| Chicken | Rabbit anti-chicken |
| Sheep | Guinea-pig anti-sheep |
| Sheep | Horse anti-sheep |
| Mouse | Rabbit anti-mouse |
| Guinea pig | Rabbit anti guinea-pig |
| Sheep | Guinea-pig anti-sheep |
| Horse | Guinea pig anti-horse |
| Beef | Guinea pig anti-beef |
| Sheep | Sheep iso-immuno-serum |
| Sheep | Goat anti-sheep |
| Cynocephalis | Rabbit anti-cynocephalis |
| Cat | Rabbit anti-cat |

*O Rh + (CD): rhesus system characterized by the presence, in the red blood cells, of pairs of allelomorphous genes called CD.

The preferred complex is formed starting from O-Rhesus negative human red blood cells and a rabbit serum containing anti-human red blood cells.

(2) Preparation of red blood cells

Sheep's blood was sampled in sterile manner on an anti-coagulating agent such as ethylene-diamine tetraacetic acid (E.D.T.A.) (known also under the name "Complexon III") in a 1 g/l solution in physiological serum (9 g/l of NaCl). Recourse may also be had to other anti-coagulating agents like for example sodium citrate.

Freshly collected cells (9 volumes per 1 volume of E.D.T.A) were immediately washed 4 times by means of physiological serum. When supernatant liquids still show hemolysis (which can be checked by means of a colorimeter at 530 mµ) one or several additional washings must be carried out.

The washed red blood cells could then either be resuspended in physiological serum to form a 10% suspension for subsequent contacting with immuno-serum or again, and preferably, be previously subjected to a pre-treatment with formol (40% formaldehyde solution) or again with any agent capable of providing tannins or substances having a tanning effect, such as by operating as follows:

(3) Preparation of formalinized red blood cells

To one volume of sheep's red blood cells suspended to between 5 and 15% (volume %) in physiological serum (solution of NaCl at 9 g/l) was added an equal volume of a formol solution i.e. a 40% formaldehyde previously neutralized to pH 7.2 by means of a normal sodium hydroxide solution diluted to between 1 and 5% in physiological serum.

The suspension was incubated under slow and constant stirring at a temperature comprised between 25° and 56° C. for twelve or twenty-two hours according to the batch. 2 or 3 washings were then carried out by means of physiological serum.

(4) Preparation of anti-sheep rabbit hemolytic serum

The sheep's fresh red blood cells prepared as described above were diluted by means of half their volume of physiological serum.

3 ml of this red blood cell suspension were injected into a rabbit 4 or 5 times at weekly intervals by the subcutaneous route followed by two injections by the intravenous route.

After checking of the serum titer, the blood of the animal was sampled by carotid puncture, one week after the last injection.

After coagulation of the blood, the serum was collected and heated to 56° C. to destroy the complement.

The serum was then preserved in sterile ampoules at +4° C.

(5) Adjustment of the titer of the hemolytic serum

Use can be made of either this rabbit anti-sheep complete hemolytic serum or of the IgG fraction which is obtained from this serum by known biochemical processes. To determine the hemagglutinating titer of the serum, a series of dilutions according to a geometrical progression of from 1/40 to 1/40000$^{th}$ was carried out under volumes of 50 µl on the hemolytic serum under study (or of the IgG fraction). A microdrop of 16 to 25 µl of a formalinized red blood cell suspension (or again, for example, of formalinized red blood cells further treated with glutaraldehyde or formalinized red blood cells further treated with tannic acid) at a weight concentration from 0.010 to 10% in a buffer close to neutral, particularly a phosphate buffer, pH 7.2 was added to each of the above said dilutes. The concentration of the red blood cells was between 0.5 and 2.5% (the volume of the red blood cell pellet measured with respect to the volume of buffer).

The titer of the serum corresponded to the inverse of the last dilution exhibing an absence of red blood cell sedimentation. The titer measured, for example 1/5000$^{th}$, corresponded to 1 hemagglutinating unit. The sensitization described hereafter of the red blood cells was carried out in the presence of an excess of antibodies of from 2 to 20 hemagglutinating units, namely corresponding to of from 1/2500$^{th}$ to 1/250$^{th}$ dilutions according to the desired sensitivity.

(6) Stabilization of the immunological complex formed by the combination of formalinized red blood cells and of anti-red blood cell antibodies of the corresponding species.

The formalinization of the red blood cells as above described was insufficient to ensure the final stability of the complex for a long period with respect to spontaneous hemagglutination, taking into account the large excess of antibodies used.

Formalinization at higher temperature, at 50° to 56° C., enabled the stabilization of the red blood cells to be improved. However to ensure stability of a very long duration it is indispensable according to the invention to subject the formalinized complex to a second treatment with another aldehydic substance such as glutaraldehyde or a substance such as tannic acid, having tanning properties (or with formaldehyde when the first stabilization treatment was made with another aldehyde or tanning agent), in the presence of albumin or of a protein having equivalent properties.

The following examples are given by way of illustration only and have no limiting character.

1ST EXAMPLE

Sheep's formalinized red blood cells, such as those obtained under (3) above were resuspended in a rabbit anti-sheep serum or the purified IgG fraction of this serum, itself diluted to a concentration of from 5 to 20 hemagglutinating units in a 7.2 phosphate buffer to form a suspension containing from 2.5 to 10, particularly from 5 to 10% of red blood cells.

To this suspension was then added one volume of a glutaraldehyde solution, at the concentration of 0.1 to 3% or of a tannic acid solution at the concentration of 0.010 to 0.05% (in weight), in a 7.2 phosphate buffer containing from 1 to 10 g/l of bovin albumin and the mixture was heated at a temperature of at least 37° C. and preferably of from about 50° C. to 56° C. for at least one hour.

The stabilized complex obtained was washed several times in 7.2 phosphate buffer containing 3 g/l of bovine albumin, then finally taken up again at the concentration of 0.5 to 2.5% in a solution of phosphate buffer of pH 7.2 to 8.2 containing bovine albumin at the concentration of 1 to 10 g/l and finally taken up again in a phosphate buffer of pH 7.2 to 8.2 containing bovine albumin at the concentration of 1 to 10 g/l and a preservation agent such as a merthioloate, notably that known under the designation MERSEPTYL at a 0.1 g/l concentration or sodium azide at a 1 g/l concentration. Other preservation agents can also be used.

A suspension of unsensitized control red blood cells was adjusted under the same conditions to form a 0.5 to 2.5% suspension in a phosphate buffer solution at a pH from 7.2 to 8.2.

2ND. EXAMPLE the formalinized red blood cells as obtained under (3) were resuspended in a phosphate buffer at pH 7.2 to form a from 2.5 to 10% suspension of red blood cells. This suspension was treated with an equal volume either of a glutaraldehyde solution at the concentration of 0.1 to 3% in phosphate buffer at pH 7.2 for at least one half hour, or with a tannic acid solution of 0.010 to 0.05% in weight in the same 7.2 pH phosphate buffer for at least one half hour, at the temperature of 37° C. Several washings with phosphate buffer then followed.

The red blood cells so obtained were resuspended in anti-sheep rabbit serum or in the previously diluted purified IgG fraction of this serum, to of from 2 to 5 hemagglutinating units, in 7.2 phosphate buffer containing of from 1 to 10 g. of bovine albumin, polyvinylpyrrolidone or gelatin per liter to form again a suspension of from 2.5 to 10% red blood cells.

The whole mixture was heated under continuous stirring for at least one half hour between 50° and 56° C.

Several washings with 7.2 phosphate buffer followed.

The immunological complex so stabilized was finally resuspended to the concentration of 0.5 to 2.5% in a phosphate buffer solution of pH 7.2 to 8.2 containing bovine albumin at the concentration of 1 to 10 g/l, or in a serum solution of a normal rabbit at the concentration of 1 to 10% (V/V) or in a MERSEPTYL solution at 0.1 g/l or sodium azide at 1 g/l.

DESCRIPTION OF THE NOVEL TECHNIQUE OF DIRECT HEMAGGLUTINATION IN MICROPLATES FOR TITRATION OF THE "RHEUMATOID FACTOR".

It is possible with the stabilized reagent according to the invention to carry out a new method of titration of the rheumatoid factor, for example on microplates of the type known under the trade name "Microtiter System".

The characteristics and advantages of the novel titrating method will emerge more clearly from the description which follows:

Microplates of plastic material provided with cylindrical recesses having conical (V-shaped) bottoms were used. It is also possible to use plates provided with recesses having U-shaped bottoms or even glass or plastic tubes having U-shaped bottoms.

For the dilutions of the serum a buffer solution of pH 6 to 8.2 was used; it is possible to use any type of known buffer, phosphate buffer, tris buffer, glycocoll buffer, with or without the addition of albumin, etc. Phosphate buffer at pH 7.2 is particularly well suited.

It is then possible to proceed as follows.

(1) A mother dilution to 1/20th of the serum to be examined was effected. 50 μl of the serum were placed in a Kahn tube for a single use and 950 μl of buffer solution were added.

(2) Volumes of 50 μl of the buffer solution were distributed by means of a micropipette in the 12 recesses of a row of a "microtiter system" plate. 50 μl of the mother dilution of the serum were added in the 1st recess and mixed with the buffer. 50 μl of the latter mixture were then transferred from the 1st recess into the second, then after mixing from the 2nd into the 3rd and so on up to the 11th recess. Finally 50 μl of the dilution formed in the 11th recess were discarded. The following dilutions were thus obtained:

| 1st | 2nd | 3rd | 4th | 5th | 6th | 7th |
|---|---|---|---|---|---|---|
| 1/40 | 1/80 | 1/160 | 1/320 | 1/640 | 1/1280 | 1/2560 |
| 8th | 9th | 10th | | 11th | | |
| 1/5120 | 1/10240 | 1/20480 | | 1/40960 | | |

50 μl of the 1/20th serum mother dilution were introduced into the 12th recess. They were mixed with an equal volume of a buffer and 50 μl were discarded. The 1/40th dilution obtained was supplemented with a microdrop (1/60th ml) of a suspension of "control red blood cells" (red blood cells which had undergone the same treatments as those contained in the control reagent, but for sensitization treatment by an anti-red blood cell immunoserum). The mixture obtained constituted a serum control. No hemagglutination should occur in the mixture obtained. A microdrop (1/60th ml) of the stabilized sensitized red blood cells reagent was deposited in the 11 other recesses.

The plate was shaken in order to ensure good homogenization and then left to stand at room temperature protected from vibrations for the whole remaining period of the test.

A reading of the plates was carried out about 2 hours later.

Interpretation of the results

Positive reactions: absence of sedimentation of red blood cells; pattern-hemagglutinations are observed.

Negative reaction: point-shaped button of sedimented red blood cells; no mat-pattern is observed.

The titer of the serum with respect to rheumatoid factor corresponded to the strongest dilution of the serum for which no sedimentation of red blood cells was observed.

The prolonged stability of the immunological complex, that is its capability of revealing the rheumatoid factor for at least two years at +4° C., enabled its standardization, according to the method described above for testing human serums, with respect to the international standard serum of rheumatoid polyarthritis of the WHO defined in Bull. Who. (S. G. ANDERSON, M. W. BENTZON, V. HOUBA, P. KRAG: International Reference Preparation of Rheumatoid Arthritis Serum, Bull. Who 42:311, 1970).

The international standard serum was obtained by dissolving 17.1 mg of the international standard in powder: in toto 100 IU in 4 ml of phosphate buffer solution at pH 7.2 to provide a solution having a 25 IU/ml concentration. The standard serum so obtained is preserved in a freezer at −20° C.

A series of 50 microliter dilutions of the standard in a 7.2 phosphate buffer was prepared like the serums studied, on microplates from ⅛th, 1/16th, 1/32th, 1/64th, 1/128th, 1/256th, 1/512th, 1/1,024th, 1/2,048th. A microdrop (1/60th ml) of the sensitized red blood cell reagent whose titer was to be determined was introduced in each recess of the microplate. The limit sensitivity threshold corresponds to the strongest dilution of the standard which still exhibits haemagglutination of the red blood cells. For example, if the limit dilution was 1/256th, the titer of the sensitized red blood cell preparation is 25:256=0.1 IU/ml, which corresponds for a serum of which the first dilution studied is 1/40th to a sensitivity of 4 IU/ml. Thus the titer of the serum in rheumatoid factor can be expressed directly in IU/ml.

Thus, for example, a limit positive reaction at 1/1,280th corresponds to 128 IU/ml, when operating a series of dilutions with a batch of stabilized reagents whose sensitivity threshold is 0.1, as is evident from the following table, in which the indicated ratios represent dilutions and the numbers indicated in IU/ml each represent corresponding concentrations of the rheumatoid factor, which would be detectable to the extent that the corresponding dilution would be representative of a "limit positive reaction".

| IU/ml | | IU/ml | |
|---|---|---|---|
| 1/40th | 4 | 1/1, 280th | 128 |
| 1/80th | 8 | ½,560th | 256 |
| 1/160th | 16 | 1/5,120th | 512 |
| 1/320th | 32 | 1/10,240th | 1,024 |
| 1/640th | 64 | 1/20,480th | 2,048 |
| | | 1/40,960th | 4,096 |

It should be mentioned that most of the occurences of the word "notably" as used herein are to be understood as "preferably" or "particularly". This applies particularly to the indications of ranges of concentrations, temperatures, pH, etc . . . , such ranges having accordingly no limitative character.

I claim:

1. Reagent for the detection of the rheumatoid factor in tests carried out in tubes or in microplates comprising an antigen-antibody complex formed from red blood cells and from antibodies against said red blood cells, said red blood cells and antibodies being immunologically fixed to each other, and said complex forming a sediment in the form of a narrow button at the tip of a tube or microtube of a microplate, when said tube or microtube terminates in a conical bottom, when said reagent is contacted in said tube or microtube with a serum free of rheumatoid factor and undergoing pattern agglutination when contacted with detectable concentrations of rheumatoid factor.

2. The reagent of claim 1, wherein the sensitivity threshold of the abovesaid complex is from 0.05 to 0.30 IU/ml.

3. The reagent of claim 1 the complex of which has a detection threshold of the rheumatoid factor in a serum diluted to 1/40, of about 0.4 to about 40 IU/ml.

4. The reagent of claim 1, wherein the detection threshold of the rheumatoid factor of the complex is from about 2 to 12 IU/ml.

5. Reagent for the detection of the rheumatoid factor in tests carried out in tubes or in microplates comprising an antigen-antibody complex formed from red blood cells and from antibodies against said red blood cells, said red blood cells and antibodies being immunologically fixed to each other, the relative content of antibodies of the complex with respect to the red blood cells providing a sensitivity threshold with respect to the international standard serum of rheumatoid polyarthritis of the WHO of about 0.01 to 1 IU/ml., and said complex forming a sediment in the form of a narrow button at the tip of a tube or microtube of a microplate, when said tube or microtube terminates in a conical bottom, when said reagent is contacted in said tube or microtube with a serum free of rheumatoid factor and undergoing pattern agglutination when contacted with detectable concentrations of Rheumatoid Factor.

6. The reagent of claim 1 or claim 5, wherein the hemagglutination titer and the agglutination titer, respectively, of the complex are in a ratio higher than 10 to 1.

7. The reagent of claim 1 or claim 5, wherein the relative content of antibodies of the complex with respect to the red cells is from about 2 to about 30 hemagglutinating units.

8. The reagent of claim 1 or claim 5, wherein the relative content of antibodies of the complex with respect to red cells is from about 3 to about 10 hemagglutinating units.

9. The reagent of claim 1 or claim 5, wherein the complex is formed from sheep red cells to which are fixed rabbit anti-sheep antibodies.

10. The reagent of claim 1 or claim 5, wherein the hemagglutination titer and the agglutination titer respectively of said complex are in a ratio of at least 20 to 1.

11. The reagent of claim 1 or claim 5, wherein the hemagglutination titer and agglutination titer respectively of said complex are in a ratio of at least 40 to 1.

12. The reagent of claim 1 or claim 5, which has a content of said complex of from 0.15 to 3% in suspension in a solution of pH from 7.2 to 8.2.

13. A process for the detection of rheumatoid factor in a biological sample which comprises contacting said biological sample in tubes or tube elements of a microplate with the reagent of claim 12 whereby said complex forms a sediment in the form of a button in the tip of said tubes or tube elements, when said tubes or tube elements terminate in a conical bottom, in the absence of detectable rheumatoid factor and undergoes pattern agglutination in the presence of detectable rheumatoid factor in said biological specimen.

14. A process for the detection of a rheumatoid factor in a biological specimen which comprises contacting said biological sample in tubes or tube elements of a microplate with the reagent of any one of claims 1, 2, 3, 4 or 5, whereby said complex forms a sediment in the form of a button in the tip of said tubes or tube elements, when said tubes or tube elements terminate in a conical bottom, in the absence of detectable rheumatoid factor and undergoes pattern agglutination in the presence of detectable rheumatoid factor in said biological specimen.

15. A process for preparing an antigen-antibody-complex of red blood cells and of antibodies against said red blood cells, wherein said red blood cells and said antibodies, are immunologically fixed to each other, which comprises subjecting said blood cells:

to distinct first and second treatments at a pH of 5 to 9.5 and at temperatures of ambient to 60° C. with an aldehyde or tanning-agent selected from the group consisting of formaldehyde, glutaraldehyde, pyruvic aldehyde, glyoxal, methyl-glyoxal, tannic acid, parabenzoquinone and sulfosalicylic acid, and to a third treatment by a dispersive substance comprising serum albumine or serum-$\alpha$- or -$\beta$-globulin at a temperature from 37° C. to 60° C.;

which process further comprises contacting said red blood cells with a sub-agglutinating dilution of said antibodies at least during the above-said first treatment and wherein the aldehyde or tanning agent used in said first treatment is distinct from the aldehyde or tanning agent used in said second treatment.

16. The process of claim 15, wherein the said treatments are carried out at a pH from 7 to 8.5 and at temperatures from 50° to 60° C., and wherein said second and third treatments are carried out simultaneously.

17. The process of claim 15, which comprises contacting said red bloods cells with a relative proportion from about 2 to about 20 hemagglutinating units of said antibodies.

18. The process of claim 17, which comprises contacting said red blood cells with from about 3 to about 10 hemagglutinating units of said antibodies.

* * * * *